US008235961B2

(12) United States Patent
Nakaoka et al.

(10) Patent No.: US 8,235,961 B2
(45) Date of Patent: Aug. 7, 2012

(54) DISPOSABLE PANTS-TYPE DIAPER

(75) Inventors: Kenji Nakaoka, Osaka (JP); Yuki Takahashi, Tsurugi-cho (JP)

(73) Assignee: Livedo Corporation, Ehime (JP)

(*) Notice: Subject to any disclaimer, the term of this patent is extended or adjusted under 35 U.S.C. 154(b) by 328 days.

(21) Appl. No.: 12/571,685

(22) Filed: Oct. 1, 2009

(65) Prior Publication Data

US 2010/0094239 A1    Apr. 15, 2010

(30) Foreign Application Priority Data

Oct. 14, 2008 (JP) ................... 2008-265548

(51) Int. Cl.
*A61F 13/15* (2006.01)
*A61F 13/20* (2006.01)

(52) U.S. Cl. ......... 604/385.27; 604/385.26; 604/385.28; 604/385.25

(58) Field of Classification Search . 604/385.25–385.27
See application file for complete search history.

(56) References Cited

U.S. PATENT DOCUMENTS

| | | | | |
|---|---|---|---|---|
| 4,323,070 A | * | 4/1982 | Ternstrom et al. | 604/385.25 |
| 4,692,163 A | * | 9/1987 | Widlund et al. | 604/385.25 |
| 4,895,568 A | * | 1/1990 | Enloe | 604/385.27 |
| 4,897,084 A | * | 1/1990 | Ternstrom et al. | 604/385.27 |
| 5,634,917 A | * | 6/1997 | Fujioka et al. | 604/385.29 |
| 5,817,087 A | | 10/1998 | Takabayashi et al. | |
| 5,836,931 A | | 11/1998 | Toyoda et al. | |
| 5,940,887 A | * | 8/1999 | Rajala et al. | 2/243.1 |
| 6,120,485 A | * | 9/2000 | Gustafsson et al. | 604/385.19 |
| 6,306,122 B1 | * | 10/2001 | Narawa et al. | 604/385.3 |
| 6,309,487 B1 | * | 10/2001 | Herrin et al. | 156/73.1 |
| 6,423,042 B1 | | 7/2002 | Sasaki | |
| 6,520,945 B1 | * | 2/2003 | Hansson | 604/385.24 |
| 6,767,344 B2 | * | 7/2004 | Suzuki | 604/385.28 |

(Continued)

FOREIGN PATENT DOCUMENTS

JP           06-296643         10/1994

(Continued)

OTHER PUBLICATIONS

European Search Report dated Feb. 15, 2010 in corresponding European Application No. 09012583.

*Primary Examiner* — Tatyana Zalukaeva
*Assistant Examiner* — Susan Su
(74) *Attorney, Agent, or Firm* — Wenderoth, Lind & Ponack, L.L.P.

(57) ABSTRACT

A disposable pants-type diaper of the present invention comprises a diaper main body including a front portion, a back portion, and a crotch portion positioned therebetween, and having a waist opening and a pair of leg openings formed by joining the front portion and the back portion; an absorbent core disposed in the crotch portion; a first elastic means disposed along an upper part of an edge of the both leg openings; and a second elastic means disposed in a middle part in a front-back direction of the crotch portion, extending in a diaper width direction to near the edge of the both leg openings, and having straight side edge portions. According to the disposable pants-type diaper of the above, a foot is hardly caught by the edge of the leg opening in wearing, resulting in easily wearing; and a fitting property of the crotch portion is excellent.

7 Claims, 8 Drawing Sheets

U.S. PATENT DOCUMENTS

| | | | |
|---|---|---|---|
| 7,094,227 B2 * | 8/2006 | Ishiguro et al. | 604/385.25 |
| 7,150,731 B2 * | 12/2006 | Cazzato et al. | 604/385.27 |
| 7,156,831 B2 * | 1/2007 | Otsubo | 604/385.27 |
| 7,226,438 B2 * | 6/2007 | Soga et al. | 604/385.25 |
| 7,410,479 B2 * | 8/2008 | Hoshino et al. | 604/385.27 |
| 2002/0049421 A1 * | 4/2002 | Hayase et al. | 604/385.27 |
| 2002/0072728 A1 * | 6/2002 | Shinohara et al. | 604/385.29 |
| 2003/0000620 A1 * | 1/2003 | Herrin et al. | 156/62.2 |
| 2003/0078556 A1 * | 4/2003 | Sasaki et al. | 604/385.25 |
| 2005/0004548 A1 * | 1/2005 | Otsubo et al. | 604/385.25 |
| 2005/0096624 A1 * | 5/2005 | Hoshino et al. | 604/385.27 |
| 2006/0064069 A1 * | 3/2006 | Rajala et al. | 604/385.24 |
| 2008/0033387 A1 * | 2/2008 | Wastlund-Karlsson et al. | 604/385.23 |
| 2008/0071241 A1 | 3/2008 | Bittner et al. | |
| 2008/0300565 A1 * | 12/2008 | Takahashi et al. | 604/367 |
| 2008/0300568 A1 | 12/2008 | Fujioka et al. | |
| 2009/0005751 A1 * | 1/2009 | Shirai et al. | 604/385.29 |
| 2009/0275911 A1 * | 11/2009 | Hormung et al. | 604/385.28 |
| 2009/0299319 A1 * | 12/2009 | Takahashi et al. | 604/385.25 |
| 2011/0015606 A1 * | 1/2011 | Nakajima et al. | 604/385.24 |
| 2011/0144610 A1 * | 6/2011 | Karlson et al. | 604/372 |

FOREIGN PATENT DOCUMENTS

| | | |
|---|---|---|
| JP | 2000-140021 | 5/2000 |
| WO | 2006/000303 | 1/2006 |

* cited by examiner

DISPOSABLE PANTS-TYPE DIAPER

BACKGROUND OF THE INVENTION

1. Field of the Invention

The present invention relates to a disposable pants-type diaper for an infant or an adult.

2. Description of the Related Art

Conventionally, there is known a disposable pants-type diaper with elastic members disposed along an edge of leg openings. For example, Japanese Laid-Open Patent Publication No. H6-296643 (Patent Document 1) discloses a disposable pants-type diaper including two elastic members disposed on front and back sides of the diaper, respectively, so that the elastic members are disposed along an entire edge of leg openings, wherein the two elastic members are disposed at a crotch portion parallel to each other and do not intersect each other at the edge of the leg openings. WO2006/000303 (Patent Document 2) discloses a disposable pants-type diaper provided with a first elastic section, a second non-elastic section, a third elastic section, and a fourth non-elastic section in this order from a longitudinal side edge of a front portion or back portion of the diaper toward a crotch center line, along an edge of leg openings, wherein the third elastic section extends across the crotch portion. Japanese Laid-Open Patent Publication No. 2000-140021 (Patent Document 3) discloses a disposable pants-type diaper including leg elastic members disposed along an edge of leg openings; and an absorbent portion elastic member disposed at a crotch portion so as to extend in a width direction and intersect the leg elastic members and an absorbent body.

Patent Documents 1 to 3 disclose disposable pants-type diapers including two elastic members disposed on the front and back sides of the diaper, respectively, and disposed at the crotch portion parallel to each other. However, when the two elastic members are disposed at the crotch portion so as to be spaced from each other, the edges of the leg openings sag at their parts between the two elastic members. Also, even when the two elastic members are disposed so as not to be spaced from each other, the edges of the leg openings sag at the crotch portion. In this case, since the elastic member is disposed continuously so as to extend along the edge of the leg openings and across the crotch portion, the elastic force in a diaper width direction and the elastic force in a leg opening periphery direction are combined at the crotch portion, and therefore, it is hard to exert an elastic force which pulls the edge of the leg opening inward in the diaper width direction at the crotch portion, resulting in sagging the edges of the leg openings at the crotch portion. If the edge of the leg opening sags, a foot is easily caught by the edge of the leg opening when the diaper is worn, causing a risk of falling down of a wearer in wearing the diaper. In addition, though such disposable pants-type diaper has sufficient leg tightness, a fitting property at a part of the crotch portion where an absorbent core is disposed is insufficient.

The present invention has been achieved in view of the above circumstances, and an object of the present invention is to provide a disposable pants-type diaper with which a foot is hardly caught by an edge of a leg opening in wearing, resulting in easily wearing, and has an excellent fitting property at a crotch portion.

SUMMARY OF THE INVENTION

A disposable pants-type diaper of the present invention which solves the above problems comprises a diaper main body including a front portion, a back portion, and a crotch portion positioned between the front portion and the back portion, and having a waist opening and a pair of leg openings formed by joining the front portion and the back portion; an absorbent core disposed in the crotch portion; a first elastic means disposed along an upper part of an edge of the both leg openings; and a second elastic means disposed in a middle part in a front-back direction of the crotch portion, extending in a diaper width direction to near the edge of the both leg openings, and having straight side edge portions. In the disposable pants-type diaper of the present invention defined as above, the second elastic means serves to pull the edge of the leg openings inward in the diaper width direction, resulting in preventing the edge of the leg openings from sagging at the middle part. Therefore, a foot is hardly caught by the edge of the leg opening in wearing the diaper, and hence the diaper is easy to wear. In addition, the crotch portion is lifted toward a wearer by an elastic force of the second elastic means, resulting in excellent in a fitting property of the crotch portion.

The disposable pants-type diaper of the present invention may further comprise at least one third elastic means disposed in the middle part in the front-back direction of the crotch portion, adjacent to and substantially parallel to the second elastic means, and having side edge portions extending upward along the edge of the leg openings, thereby providing a non-elastic region along the edge of the leg openings between the first elastic means and the third elastic means. The non-elastic region formed between the first elastic means and the third elastic means prevents the first and third elastic means from excessively tightening a leg of a wearer, and improves a wearing feel around the leg. Preferably, the four first elastic means are disposed along the upper parts of the edges of the both leg openings, and the two third elastic means are disposed adjacent to the second elastic means at front and back sides respectively, thereby forming the four non-elastic regions along the edge of the both leg openings.

In the disposable pants-type diaper of the present invention, the first elastic means may be disposed continuously so as to extend across the crotch portion and along the edge of the both leg openings. In the embodiment according to the above, the edge of the leg opening does not sag at the middle part, and therefore, a foot is hardly caught by the edge of the leg opening in wearing, resulting in easily wearing. In addition, the crotch portion is lifted toward a wearer by the elastic force of the second elastic means, resulting in excellent in the fitting property of the crotch portion.

The disposable pants-type diaper of the present invention is easy to wear, because a foot is hardly caught by the edge of the leg opening in wearing. In addition, in the disposable pants-type diaper of the present invention, the crotch portion is lifted toward a wearer, resulting in excellent in the fitting property of the crotch portion.

DESCRIPTION OF THE PREFERRED EMBODIMENTS

A disposable pants-type diaper of the present invention comprises a diaper main body containing a front portion, a back portion, and a crotch portion positioned between the front portion and the back portion. The diaper main body has a waist opening and a pair of leg openings formed by joining the front portion and the back portion. Specifically, the front portion and the back portion are joined at their side edge portions in a diaper width direction to form the pair of leg openings on both sides of the crotch portion and the waist opening provided by end portions, with respect to a diaper front-back direction, of the front and back portions.

Concerning the name of each part of the diaper man body, a part applied to an abdomen side of a wearer is called the front portion, a part applied to a buttocks side of the wearer is called the back portion, and a part positioned between the front portion and the back portion and applied to a crotch of the wearer is called the crotch portion, in a state of wearing the disposable pants-type diaper. The crotch portion is the middle position when the diaper main body is divided into three parts in the diaper front-back direction in a state that the front portion and the back portion of the disposable pants-type diaper are disjoined and the diaper main body is developed on a plane, and the crotch portion is a part whose side edge portions in the diaper width direction are not joined when the diaper is formed in the shape of pants. Thus, the leg openings are formed only on both sides of the crotch portion.

The diaper front-back direction means a direction from the front portion toward the back portion of the disposable pants-type diaper. The diaper width direction means a direction orthogonal to the front-back direction on the same plane as the disposable pants-type diaper.

The disposable pants-type diaper of the present invention comprises an absorbent core disposed in the crotch portion of the diaper main body. The absorbent core is present at least in the crotch portion, and further, may be also extended to the front portion and/or the back portion.

In one embodiment of the diaper main body provided with the absorbent core, for example, a laminate comprising a liquid-permeable top sheet, a liquid-impermeable back sheet, and the absorbent core interposed therebetween may contain the front portion, the back portion and the crotch portion therebetween. Here, the top sheet is preferably liquid-permeable, and the back sheet is preferably liquid-impermeable or water-repellent.

In another embodiment of the diaper main body provided with the absorbent core, the diaper main body containing the front portion, the back portion, and the crotch portion therebetween may be formed from a laminate comprising an inner sheet and an outer sheet; and an absorbent body in which the absorbent core is interposed between a liquid-permeable top sheet and a liquid-impermeable back sheet may be provided on the surface of the inner sheet on a wearer's side. Here, the inner sheet is preferably liquid-permeable, and the outer sheet is preferably hydrophilic or water-repellent.

The absorbent core is not particularly limited as long as it absorbs excrement such as urine and the like, however, it preferably contains an absorbent polymer resin. The absorbent core can be obtained, for example, by the steps of mixing a hydrophilic fiber assembly layer such as crushed pulp fiber, cellulose fiber and the like with a granular absorbent polymer resin to obtain a clump; wrapping the clump with a paper sheet such as a tissue paper and the like, or with a cover sheet such as a liquid-permeable nonwoven fabric sheet and the like; and molding the obtained wrapped clump into a pre-defined shape such as a rectangular shape, a hourglass shape, a center nipped-in gourd shape, a battledore shape, and the like.

Rising flaps are preferably provided along an edge of opposite side, with respect to the diaper width direction, of the absorbent core. For example, the rising flaps may be provided on the upper surface of the absorbent core at side edge parts thereof in the width direction, or outside the absorbent core in the width direction. In the embodiment that the absorbent core is interposed between the top sheet and the back sheet, the rising flaps are joined, for example, to the top sheet. The rising flaps are preferably made of a liquid-impermeable plastic film, a water-repellent nonwoven fabric, or the like, and more preferably made of a water-repellent nonwoven fabric. Providing the rising flaps enables to prevent lateral leakage of urine and the like.

An elastic member for erection is preferably provided at each of upper edge parts (edge parts on a wearer side) of the rising flaps that are in a rising state. Rising gathers which rises toward a wearer are formed by a shrinkage force of the elastic member for erection, thereby preventing lateral leakage of urine and the like. The inner surfaces of the rising flaps may be joined to the top sheet at end parts in the diaper front-back direction of the rising flaps, thereby preventing leakage of urine and the like in the front-back direction.

The disposable pants-type diaper of the present invention comprises a first elastic means disposed along an upper part of an edge of the both leg openings. The first elastic means is preferably attached to the diaper main body in a stretched state. The first elastic means may be disposed either continuously or discontinuously, however, it is preferably disposed continuously. The first elastic means forms leg gathers around a leg of a wearer, resulting in preventing leakage of excrement such as urine and the like from the crotch portion.

Here, the term "upward" means a direction from a bottom of the crotch portion toward the waist opening in a state that the diaper is formed in the shape of pants, and the term "upper part" means a side nearer to the waist opening in the above state. On the other hand, the term "downward" means a direction from the waist opening toward the bottom of the crotch portion in a state that the diaper is formed in the shape of pants, and the term "lower part" means a side nearer to the bottom of the crotch portion in the above state.

In the present invention, the crotch portion of the diaper main body is divided into three parts in the diaper front-back direction, a part on a front side of the crotch portion is referred to as a front crotch part, a part on a back side of the crotch portion is referred to as a back crotch part, and a part between the front crotch part and the back crotch part is referred to as a middle part. Therefore, the upper part of the edge of the leg opening means parts of the edge of the leg opening at the front crotch part and the back crotch part. Thus, it can be said that the first elastic means is disposed along the edge of the both leg openings at the front crotch part and/or the back crotch part.

The first elastic means may be also disposed in the front portion and/or the back portion. Preferably, the first elastic means extends to a part where the front portion and the back portion are joined, and is disposed along the entire edge of the leg openings except the middle part. However, the first elastic means is not disposed in the middle part.

The first elastic means disposed along the edge of the leg openings is generally located at 5 mm or more inward from the edge of the leg openings, and hence blank spaces are provided along the edge of the leg openings.

The first elastic means may comprise one or a plurality of elastic members, however, preferably comprises 2 to 10 elastic members. In the case that the first elastic means comprises a plurality of elastic members, even if one elastic member is broken, the leg gather can be maintained by the remaining elastic members. In addition, by disposing a plurality of elastic members side by side, wearing feel around a leg can be made soft while a high stretching force is maintained.

The disposable pants-type diaper of the present invention comprises a second elastic means disposed in the middle part in the front-back direction of the crotch portion, extending in a diaper width direction to near the edge of the both leg openings, and having straight side edge portions. That is, the second elastic means is disposed in the middle part in the front-back direction of the crotch portion so as to extend in a diaper width direction to near the edge of the both leg openings, and has straight side edge portions. The second elastic means is preferably attached to the diaper main body in a stretched state.

Since the second elastic means extends in the diaper width direction to near the edge of the both leg openings and has the straight side edge portions extending in the diaper width direction, a force which pulls the edges of the leg openings inward in the diaper width direction is exerted at the middle part of the crotch portion. As a result, the edge of the leg opening does not sag at the middle part. Therefore, when the disposable pants-type diaper of the present invention is worn, a foot is hardly caught by the edge of the leg opening, and hence the diaper is easy to wear.

Further, in the disposable pants-type diaper of the present invention, since an elastic force of the second elastic means acts in the diaper width direction, the crotch portion is lifted toward a wearer by the elastic force of the second elastic means, resulting in excellent in a fitting property of the crotch portion. On the other hand, if the second elastic means is not disposed, the crotch portion tends to sag.

The both side edge portions of the second elastic means are located preferably in an area within preferably 15 mm, more preferably 10 mm, and even more preferably 5 mm from the edge of the leg openings. When the both side edge portions of the second elastic means are located in the area within 15 mm from the edge of the leg openings, the effect of preventing the edge of the leg openings from sagging at the middle part is ensured. In addition, the second elastic means preferably extends so as to be closer to the edge of the leg openings than the first elastic means and later-described third elastic means. The side edge portions of the second elastic means are preferably located in the area of 0.5 mm or more away from the edge of the leg openings. When the side edge portions of the second elastic means are located in the areas of 0.5 mm or more away from the edge of the leg openings, the edge of the leg openings is hardly jagged even though the edge of the leg opening is pulled inward in the diaper width direction by the elastic force of the second elastic means, resulting in an excellent feel of the edge against a wearer.

The second elastic means may be disposed either continuously or discontinuously as long as disposed near the edge of the leg openings in the diaper width direction. However, in order to prevent the edge of the leg openings from sagging at the middle part and to maximize the effect of lifting the crotch portion toward a wearer, the second elastic means is preferably continuously disposed. More preferably, the second elastic means is continuously disposed such that the entirety thereof extends linearly in the diaper width direction.

The second elastic means may comprise one or a plurality of elastic members, however, preferably comprises a plurality of elastic members. In the case that the second elastic means comprises a plurality of elastic members, the respective elastic members are preferably arranged substantially parallel to each other. In addition, in the case that the second elastic means comprises a plurality of elastic members, intervals among the elastic members are preferably substantially the same. When the elastic members constituting the second elastic means are arranged substantially parallel to each other, the elastic force of the second elastic means is exerted at its maximum. When the intervals among the elastic members constituting the second elastic means are substantially the same, the elastic force is evenly exerted on a region where the second elastic means is disposed of the crotch portion, thereby ensuring the effect of preventing the edge of the leg openings from sagging at the middle part and improving the fitting property of the crotch portion.

Thus, when the second elastic means comprises a plurality of elastic members, the respective elastic members are preferably disposed such that the entirety thereof extends linearly in the diaper width direction and the elastic members are substantially parallel to each other at a substantially uniform interval.

When the second elastic means comprises a plurality of elastic members, the number of the elastic members constituting the second elastic means is preferably 2 or more and more preferably 3 or more, and preferably 10 or less and more preferably 5 or less. When the number of the elastic members constituting the second elastic means is 2 or more, the edge of the leg openings is less likely to sag at the middle part and the fitting property of the crotch portion is improved easily. On the other hand, when the number of the elastic members constituting the second elastic means exceeds 10, the effect of the second elastic means is not improved markedly and the production becomes difficult, resulting in increased production cost. Thus, the number of the elastic members constituting the second elastic means is preferably 10 or less.

When the second elastic means comprises a plurality of elastic members, the intervals among the elastic members are preferably 0.5 mm or more and more preferably 1 mm or more, and preferably 10 mm or less and more preferably 7 mm or less. When the intervals among the elastic members are 0.5 mm or more, the elastic members are not excessively densely disposed, and hence the flexibility of the crotch portion is ensured. When the intervals among the elastic members are 10 mm or less, the edge of the leg openings is less likely to sag at the middle part and the fitting property of the crotch portion is improved easily.

In the case that the second elastic means comprises a plurality of elastic members, a distance between a frontmost elastic member and a rearmost elastic member in the diaper front-back direction is 0.5 mm or more and more preferably 1 mm or more, and preferably 90 mm or less and more preferably 40 mm or less. When the distance between the frontmost elastic member and the rearmost elastic member is 0.5 mm or more, an area where the second elastic means is disposed in the crotch portion is ensured sufficiently, and hence the edge of the leg openings is less likely to sag at the middle part and the fitting property of the crotch portion is improved easily. When the distance between the frontmost elastic member and the rearmost elastic member is 90 mm or less, the leg gathers are formed sufficiently around a leg, resulting in easily preventing leakage of excrement such as urine and the like from the crotch portion.

In the case that the second elastic means is disposed adjacent to the first elastic means, the second elastic means is preferably disposed so as to be spaced from the first elastic means in the diaper front-back direction. In order to cause the elastic force of the second elastic means to be exerted at its maximum, the first elastic means and the second elastic means preferably neither contact nor intersect each other.

In the case that the second elastic means is disposed adjacent to the first elastic means, a distance between the second elastic means and the first elastic means is not particularly limited. However, the distance between the second elastic means and the first elastic means is preferably 0.5 mm or more and more preferably 1 mm or more, and preferably 10 mm or less and more preferably 7 mm or less. When the distance between the second elastic means and the first elastic means is 0.5 mm or more, the force of the second elastic means which pulls the edge of the leg openings inward in the diaper width direction is hardly impaired by the first elastic means, and therefore the edge of the leg openings is less likely to sag at the middle part. When the distance between the second elastic means and the first elastic means is 10 mm or less, sagging of the edge of the leg openings which is caused due to an excessively increased distance between the second elastic means and the first elastic means is less likely to occur. Here, the distance between the second elastic means and the first elastic means means the shortest distance between the elastic members of the second elastic means and the first elastic means.

The second elastic means is disposed in the middle part in the front-back direction of the crotch portion, and the middle part may be located in the center of the crotch portion in the front-back direction, or may not be located in such a position. The middle part may be unevenly located toward the front or back side of the crotch portion. For example, when the second elastic means is unevenly located toward the front side of the crotch portion, the fitting property in the vicinity of genitals is enhanced, resulting in enhancing the effect of preventing leakage of urine and the like easily.

Next, another embodiment of the disposable pants-type diaper of the present invention is explained. The disposable pants-type diaper of the present invention may further comprise at least one of third elastic means disposed in the middle part in the front-back direction of the crotch portion, adjacent to and substantially parallel to the second elastic means, and having side edge portions extending upward along the edge of the leg openings, thereby providing a non-elastic region along the edge of the leg openings between the first elastic means and the third elastic means. That is to say, the third elastic means is disposed adjacent to the second elastic means at the front and/or back side of the second elastic means, and is disposed between the first elastic means and the second elastic means so as to be spaced therefrom in the diaper front-back direction. And further, the third elastic means is disposed such that side edge portions thereof extend upward along the edge of the leg openings and a middle portion thereof extends in the diaper width direction.

Since the side edge portions of the third elastic means extend upward along the edge of the leg openings, the side edge portions of the third elastic means cooperate with the first elastic means to form the leg gathers around a leg of a wearer. As a result, leakage of excrement such as urine and the like from the crotch portion is prevented.

The part extending in the diaper width direction of the third elastic means serves to lift the crotch portion toward a wearer, resulting in improving the fitting property of the crotch portion. In addition, since the third elastic means is disposed so as not to contact and intersect the second elastic means, the elastic force of the second elastic means is exerted at its maximum.

It is sufficient that the third elastic means has a part that is adjacent to and substantially parallel to the second elastic means as a part thereof, however, the part of the third elastic means, that is adjacent to and substantially parallel to the second elastic means, is preferably greater. When the greater part of the third elastic means is disposed adjacent to and substantially parallel to the second elastic means, the effect that the third elastic means cooperates with the second elastic means to lift the crotch portion toward a wearer is enhanced.

The part extending in the diaper width direction of the third elastic means may be disposed, for example, in a linear shape, in a curved shape so as to be convex on the second elastic means side, or in the shape of a combination of them.

The part extending in the diaper width direction of the third elastic means is preferably disposed such that the greater part thereof is substantially parallel to the second elastic means. Further, since the second elastic means is preferably disposed such that the entirety thereof extends linearly in the diaper width direction, the part extending in the diaper width direction of the third elastic means is preferably disposed such that the greater part thereof extends linearly in the diaper width direction. The part extending in the diaper width direction of the third elastic means is preferably disposed such that, for example, a part extending linearly in the diaper width direction covers 10% or more and more preferably 30% or more of a width of the crotch portion.

The part disposed along the edge of the leg openings of the third elastic means is generally located at 5 mm or more inward from the edge of the leg openings, and hence blank spaces are provided along the edge of the leg openings.

The third elastic means is preferably attached to the diaper main body in a stretched state. The third elastic means may be disposed either continuously or discontinuously, however, it is preferably disposed continuously, because the fitting property around a leg is ensured and the fitting property of the crotch portion is improved.

The third elastic means may comprise one or a plurality of elastic members, however, preferably comprises 2 to 10 elastic members. In the case the third elastic means comprises a plurality of elastic members, even if one elastic member is broken, the leg gather and the effect of lifting the crotch portion toward a wearer can be maintained by the remaining elastic members. In addition, by disposing a plurality of elastic members side by side, wearing feel around a leg can be made soft while a high stretching force is maintained.

The non-elastic region formed between the first elastic means and the third elastic means prevents the first elastic means and the third elastic means from excessively tightening legs of a wearer, and improves the wearing feel around the leg. Generally, when an elastic member is provided along the edge of the leg opening, it is concerned that a non-elastic region provided at a part of the edge of the leg opening causes loosing the lower part of the crotch portion to separate from a skin of a wearer easily, resulting in deterioration of the fitting property of the crotch portion. However, in the present invention, since the second elastic means is provided, the fitting property of the crotch portion and the wearing feel around a leg can be improved simultaneously in spite of presence of the non-elastic region provided between the first elastic means and the third elastic means.

The position of the non-elastic region along the edge of the leg openings formed between the first elastic means and the third elastic means is not particularly limited as long as it is a position along the edge of the leg openings where the second elastic means is not disposed. For example, the third elastic means is preferably disposed so as to have a length of 15 mm to 80 mm (preferably, 20 mm to 75 mm) in the diaper front-back direction, and the non-elastic region is preferably formed on an upper side to the third elastic means of above described position.

The length of the non-elastic region, that is the distance between a lower end of the first elastic means and an upper end of the third elastic means, is not particularly limited, however, it is preferably 20 mm or more and more preferably 30 mm or more, and preferably 60 mm or less and more preferably 50 mm or less. When the length of the non-elastic region is 20 mm or more, the wearing feel around a leg is improved easily, while when the length of the non-elastic region is 60 mm or less, a part where the leg gather is not formed is not excessively extended, resulting in forming the leg gather appropriately.

In the disposable pants-type diaper of the present invention, the four first elastic means are preferably disposed along the upper parts of the edges of the both leg openings, and the two third elastic means are preferably disposed adjacent to the second elastic means at front and back sides respectively, thereby forming the four non-elastic regions along the edge of the both leg openings. When the four non-elastic regions are formed along the edge of the leg openings, leg gathers are formed around both legs on the front and back sides appropriately, resulting in improving the wearing feel around legs.

The third elastic means is disposed adjacent to the second elastic means, and a distance between the third elastic means and the second elastic means is not particularly limited. However, the distance between the third elastic means and the second elastic means is preferably 0.5 mm or more and more preferably 1 mm or more, and preferably 10 mm or less and more preferably 7 mm or less. When the distance between the third elastic means and the second elastic means is 0.5 mm or more, the elastic members are not excessively densely disposed, and hence the flexibility of the crotch portion is ensured easily. When the distance between the third elastic means and the second elastic means is 10 mm or less, the fitting property of the crotch portion is improved easily. Here, the distance between the third elastic means and the second elastic means is the shortest distance between the elastic members of the third elastic means and the second elastic means.

In the case that the second elastic means comprises a plurality of elastic members, the distance between the third elastic means and the second elastic means is preferably shorter than the intervals among the respective elastic members of the second elastic means. The length of the part extending in the diaper width direction of the third elastic means tends to be shorter than that of the second elastic means, and therefore, in this case, the elastic force of the third elastic means in the diaper width direction becomes smaller than that of the second elastic means. However, when the distance between the third elastic means and the second elastic means is shorter than the intervals among the respective elastic members of the second elastic means, the third elastic means and the second elastic means cooperate to lift the crotch portion toward a wearer easily, resulting in improving the fitting property of the crotch portion.

A method of forming the non-elastic region is not particularly limited. For example, the non-elastic region may be formed by independently providing the first elastic means and the third elastic means so as to be spaced from each other in the diaper front-back direction. However, the first elastic means, the third elastic means and the non-elastic region are preferably formed by providing an elastic member continuously so as to extend across the crotch portion and along the edge of the both leg openings, and cutting the elastic member positioned along the edge of the leg openings. According to such a manner, the first and third elastic means are easily disposed in manufacturing while forming the non-elastic regions easily.

A method of cutting the elastic member is not particularly limited, and for example, a method of physically cutting with a cutter, a scissors, or the like and a method of cutting with heat or laser light are exhibited. As a method of cutting the elastic member, the method of cutting the elastic member with a cutter is preferred, because it is simple and easy. The number of cutting positions may be 1 or more. The elastic member may be also cut at a plurality of positions to form one non-elastic region. The number of the cutting positions is not particularly limited as long as the non-elastic region is formed by cutting. Preferably, the elastic member is dot-cut by using a roll equipped with a plurality of cutters.

As described above, in the disposable pants-type diaper of the present invention, the first elastic means and the second elastic means are provided essentially, and the third elastic means is provided according to need. The second elastic means serves to prevent the edge of the leg openings from sagging at the middle part and to lift the crotch portion toward a wearer to enhance the fitting property of the crotch portion. The effect of preventing the edge of the leg openings from sagging at the middle part is described in detail below.

If the disposable pants-type diaper does not have the second elastic means and only the first elastic means are disposed along the upper part of the edge of the leg openings, a part of the edge of the leg openings where the first elastic means is deposed are less likely to sag due to the elastic force in the leg opening periphery direction of the elastic member of the first elastic means. However, since the first elastic means does not generate an elastic force in a direction so as to pull the edge of the leg openings, that is inward in the diaper width direction, the edge of the leg openings sags at the middle part where the first elastic means is not present.

Even when the disposable pants-type diaper further has the third elastic means but not has the second elastic means, the edge of the leg openings sag at the middle part. The third elastic member has the side edge portions extending upward along the edge of the leg openings, and therefore, though the third elastic means has the part extending in the diaper width direction, the elastic force in the diaper width direction of this part is combined with the elastic force in the leg opening periphery direction of the side edge portion in the vicinity of the edge of the leg openings, resulting in hardly exerting an elastic force which pulls the edge of the leg openings inward in the diaper width direction. Thus, even in the embodiment that the third elastic means is provided, the edge of the leg openings sag at the middle part.

On the other hand, in the disposable pants-type diaper of the present invention, the second elastic means is disposed in the middle part of the crotch portion so as to extend in the diaper width direction. Since the second elastic means extends in the diaper width direction to near the edge of the leg openings and has the straight side edge portions, an elastic force which pulls the edges of the leg openings inward in the diaper width direction is exerted at the middle part of the crotch portion, resulting in preventing the edge of the leg openings from sagging at the middle part. Therefore, when the disposable pants-type diaper of the present invention is worn, a foot is hardly caught by the edge of the leg opening, and hence the diaper is easy to wear.

Next, yet another embodiment of the disposable pants-type diaper of the present invention is explained. In the disposable pants-type diaper of the present invention, the first elastic means may be disposed continuously so as to extend across the crotch portion and along the edge of the both leg openings. In this embodiment, it is preferable that the third elastic means is not disposed.

The first elastic means is preferably disposed adjacent to the second elastic means at the front and/or back side of the second elastic means. More preferably, two first elastic means are disposed adjacent to the second elastic means at the front and back sides of the second elastic means, respectively.

A part extending across the crotch portion of the first elastic means is preferably disposed so as to be adjacent to and substantially parallel to the second elastic means. The conditions and effects of providing the part extending across the crotch portion of the first elastic means are the same as the preferable conditions and effects of providing the third elastic means (specifically, the part extending in the diaper width direction of the third elastic means).

Also in the disposable pants-type diaper in this embodiment, the edge of the leg openings do not sag at the middle part, and a foot is hardly caught by the edge of the leg opening in wearing, resulting in easily wearing. In addition, the crotch portion is lifted toward a wearer by the elastic force of the second elastic means, resulting in excellent in the fitting property of the crotch portion.

In the disposable pants-type diaper of the present invention, the first elastic means and the second elastic means disposed essentially and the third elastic means disposed according to need are preferably attached between two sheets.

For example, when the diaper main body is composed of a laminate comprising a liquid-permeable top sheet, a liquid-impermeable back sheet, and an absorbent core interposed therebetween, each elastic member is preferably attached between the top sheet and the back sheet. Here, at a part where the absorbent core is present, each elastic member is preferably provided between the absorbent core and the back sheet. In this case, each elastic member may be joined to the back sheet, and at least the second elastic means may not be joined to the absorbent core. For example, the first and third elastic means are joined to the absorbent core and the back sheet, and the second elastic means is joined to the back sheet, but not joined to the absorbent core. When the second elastic means is not joined to the absorbent core, the elastic force in the diaper width direction of the second elastic means is not prevented by a rigidity of the absorbent core, thereby more effectively preventing the edge of the leg openings from sagging at the middle part.

For example, when the diaper main body is composed of a laminate comprising an inner sheet and an outer sheet; and an absorbent body in which an absorbent core is interposed between a top sheet and a back sheet is provided on the surface of the inner sheet on a wearer side, each elastic member is preferably provided between the inner sheet and the outer sheet. In this case, the absorbent body may not be joined to a part of the diaper main body where the second elastic means is attached. When the absorbent body is not joined to the part of the diaper main body where the second elastic means is attached, the elastic force in the diaper width direction of the second elastic means is not prevented by a rigidity of the absorbent core, thereby more effectively preventing the edge of the leg openings from sagging at the middle part.

The disposable pants-type diaper of the present invention may further comprise a waist elastic member disposed along an edge of the waist opening, and a body elastic member disposed in the front portion and the back portion so as to extend in the diaper width direction, in addition to the first to third elastic means. The waist elastic member prevents excrement such as urine and the like from leaking from a back side or an abdomen side, even when a wearer lies. The body elastic member improves the fitting property of the diaper around an abdomen region. The waist elastic member and the body elastic members are preferably attached between two sheets, similarly to the first to third elastic means.

Elastic materials such as a polyurethane thread, a polyurethane film, a natural rubber, and the like, which are generally used for disposable diapers, can be used for each elastic member. Each elastic member is preferably attached in a stretched state on a sheet or between sheets by bonding means such as a hot-melt adhesive agent, heat bonding, ultrasonic bonding, and the like. For example, a polyurethane thread with a size of 100 dtex to 2,500 dtex is stretched at a ratio of 1.1 to 5.0 times to be provided. The preferable bonding means is a rubber-based hot-melt adhesive agent.

An example of the disposable pants-type diaper of the present invention is explained, referring to drawings. However, the present invention is not restricted to the following embodiment.

Figure 1:
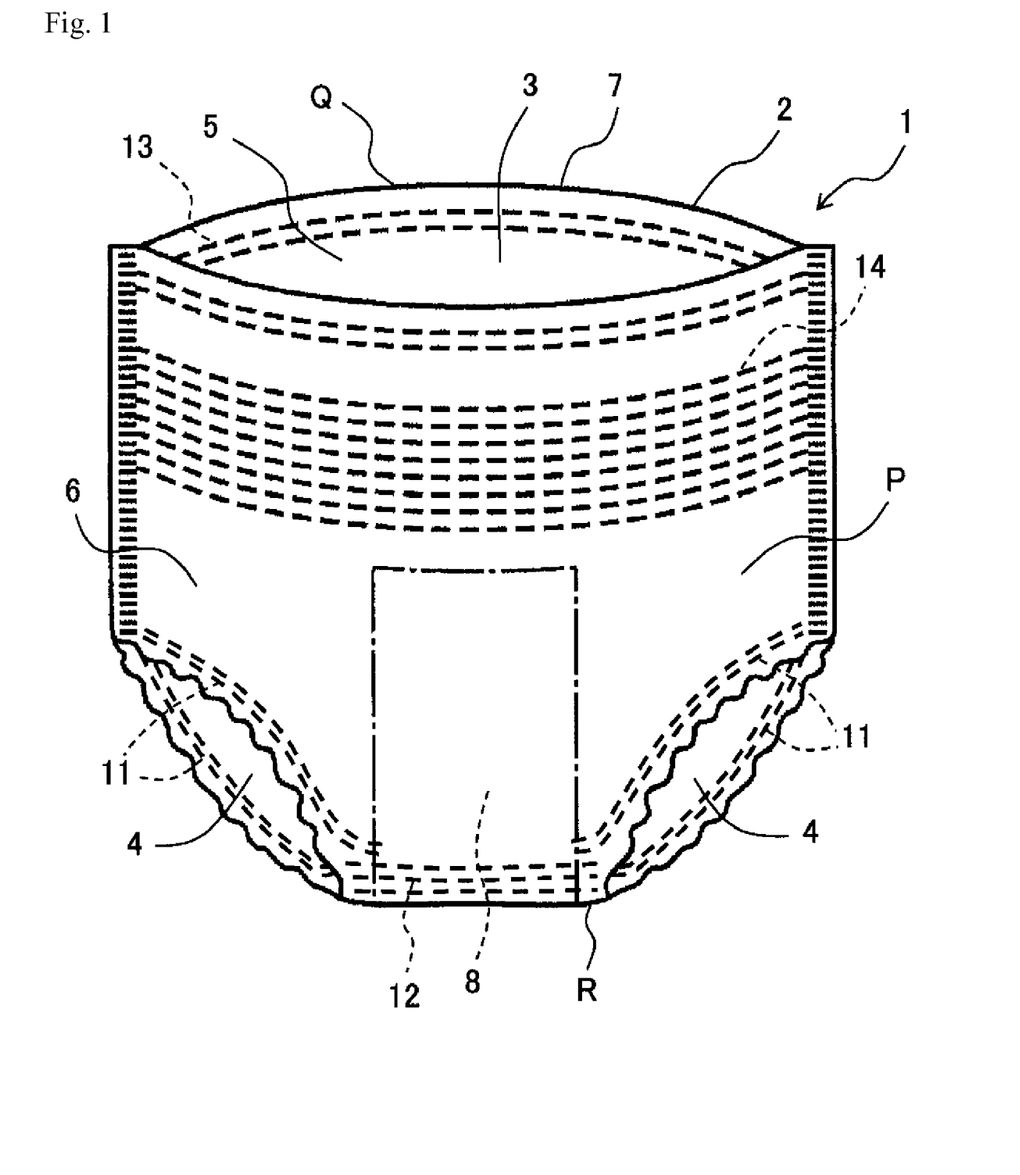
FIG. 1 shows a perspective view of a disposable pants-type diaper of the present invention according to a first embodiment.
Figure 2:
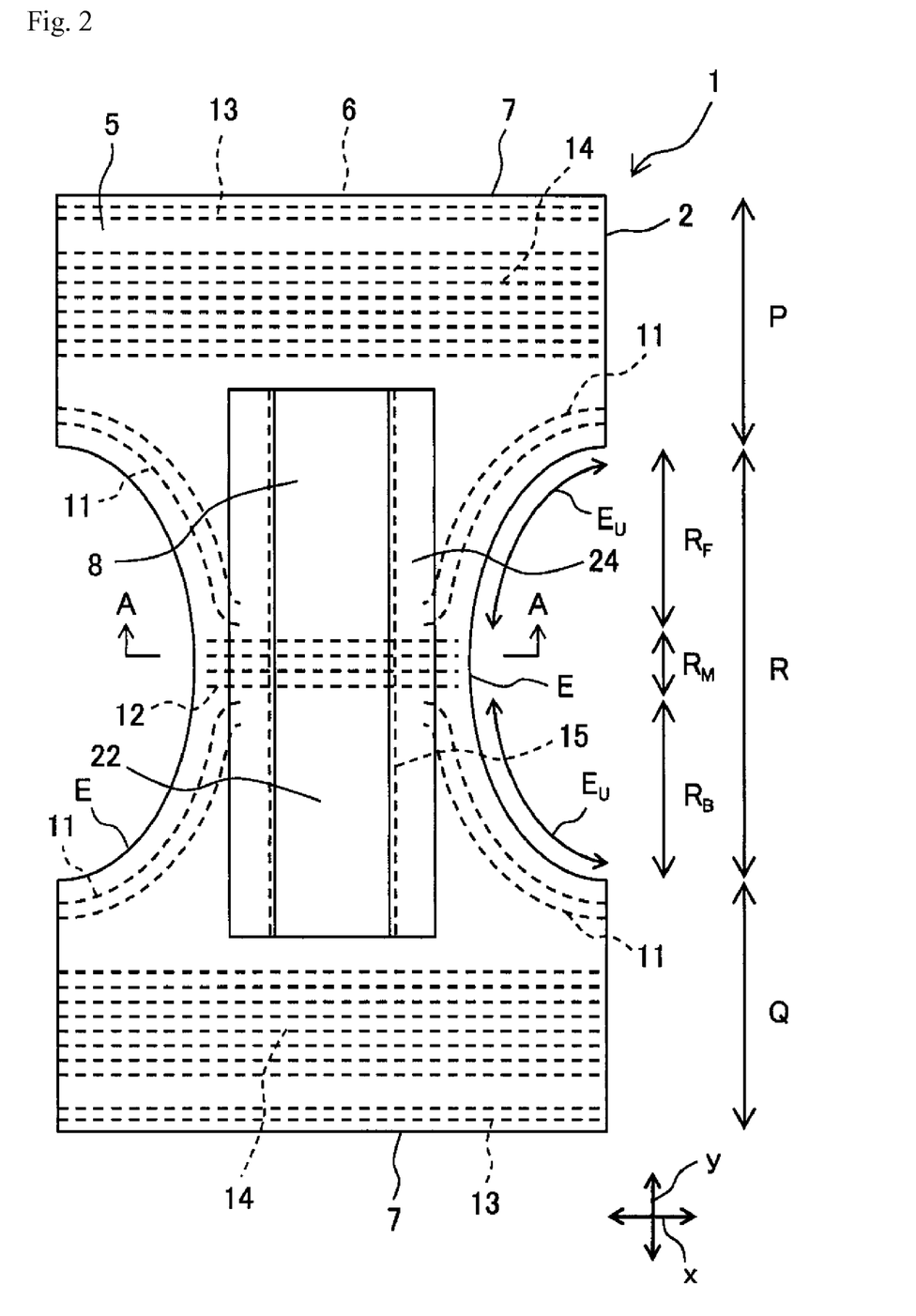
FIG. 2 shows a plan view of the disposable pants-type diaper shown in FIG. 1 in a developed state in which a front portion and a back portion are disjoined.
Figure 3:
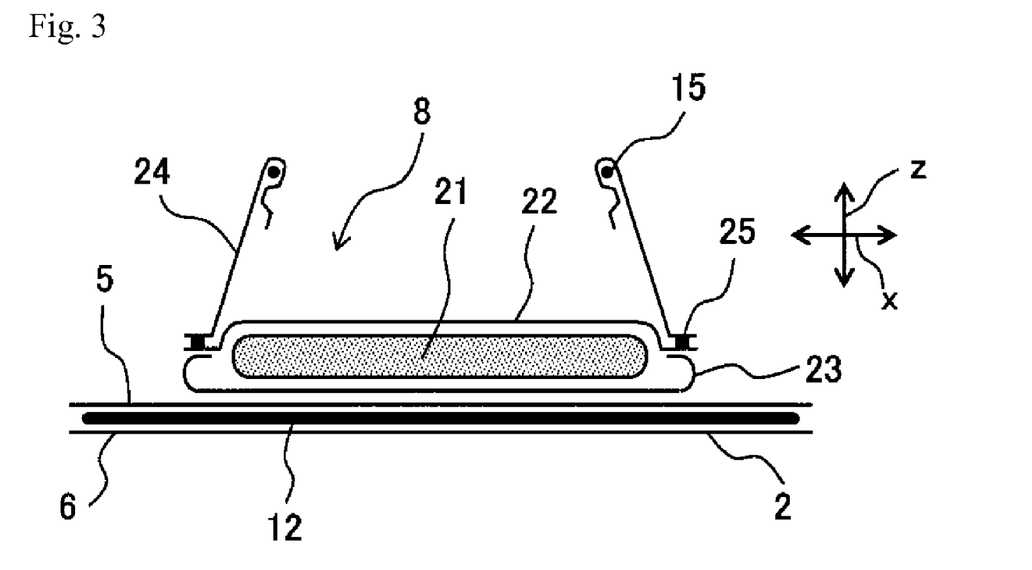
FIG. 3 shows a cross-sectional view taken along the line A-A in FIG. 2.

A first embodiment of the disposable pants-type diaper of the present invention is explained referring to FIGS. 1 to 3. The disposable pants-type diaper according to the first embodiment comprises a first elastic means disposed along an upper part of an edge of both leg openings; and a second elastic means disposed in a middle part in a front-back direction of a crotch portion, extending in a diaper width direction to near the edge of the both leg openings, and having straight side edge portions.

FIG. 1 shows a perspective view of the disposable pants-type diaper of the present invention according to the first embodiment. FIG. 2 shows a plan view of the disposable pants-type diaper shown in FIG. 1 in a developed state in which a front portion and a back portion are disjoined. FIG. 3 shows a cross-sectional view taken along the line A-A in FIG. 2. In FIG. 2, the arrow x direction is defined as the diaper width direction, and the arrow y is defined as the diaper front-back direction. In addition, the direction perpendicular to the plane formed by the arrows x and y is defined as a thickness direction z.

The disposable pants-type diaper 1 comprising a diaper main body 2 including a front portion P, a back portion Q, and a crotch portion R positioned between the front portion P and the back portion Q. The crotch portion R is divided in the diaper front-back direction y, thereby providing a front crotch part $R_F$, a back crotch part $R_B$, and a middle part $R_M$ therebetween. The diaper main body 2 is formed by joining the front portion P and the back portion Q, thereby forming a waist opening 3 and a pair of leg openings 4. The diaper main body 2 is a laminate composed of an inner sheet 5 and outer sheet 6.

First elastic means 11 are disposed along the edge E of the leg openings 4 at the front crotch part $R_F$ and the back crotch part $R_B$, that is along the upper parts $E_u$ of the edge E of the leg openings 4. A second elastic means 12 is disposed in the middle part $R_M$ in the front-back direction of the crotch portion R, extends in the diaper width direction x to near the edge E of the leg openings 4, and has straight side edge portions. The first elastic means 11 and the second elastic means 12 are attached between the inner sheet 5 and the outer sheet 6 in a stretched state.

A waist elastic member 13 is disposed along an edge 7 of the waist opening 3. Body elastic members 14 are disposed in the front portion P and the back portion Q so as to extend in the diaper width direction x. The waist elastic member 13 and the body elastic members 14 are attached between the inner sheet 5 and the outer sheet 6 in a stretched state.

The crotch portion R is provided with an absorbent core 21 (FIG. 3). The absorbent core 21 is interposed between a liquid-permeable top sheet 22 and a liquid-impermeable back sheet 23 to form an absorbent body 8. The absorbent body 8 is not joined to the diaper main body 2 at a part where the second elastic means 12 is attached (the middle potion $R_M$ in FIG. 2), however, it is joined to the diaper main body 2 at some part other than the above part.

Rising flaps 24 are provided along an edge of opposite sides, with respect to the diaper width direction x, of the absorbent core 21. The rising flaps 24 are joined to the top sheet 22 at fixing portions 25, and extend in the diaper front-back direction y. Rising gathers which rises upward (toward a wearer) are formed from the rising flaps 24 by shrinkage forces of elastic members for erection 15, thereby preventing lateral leakage of urine and the like. The inner surfaces of the rising flaps 24 are joined to the top sheet 22 at front and back end parts of the absorbent body 8, thereby preventing leakage of urine and the like in the front-back direction y.

Figure 4:
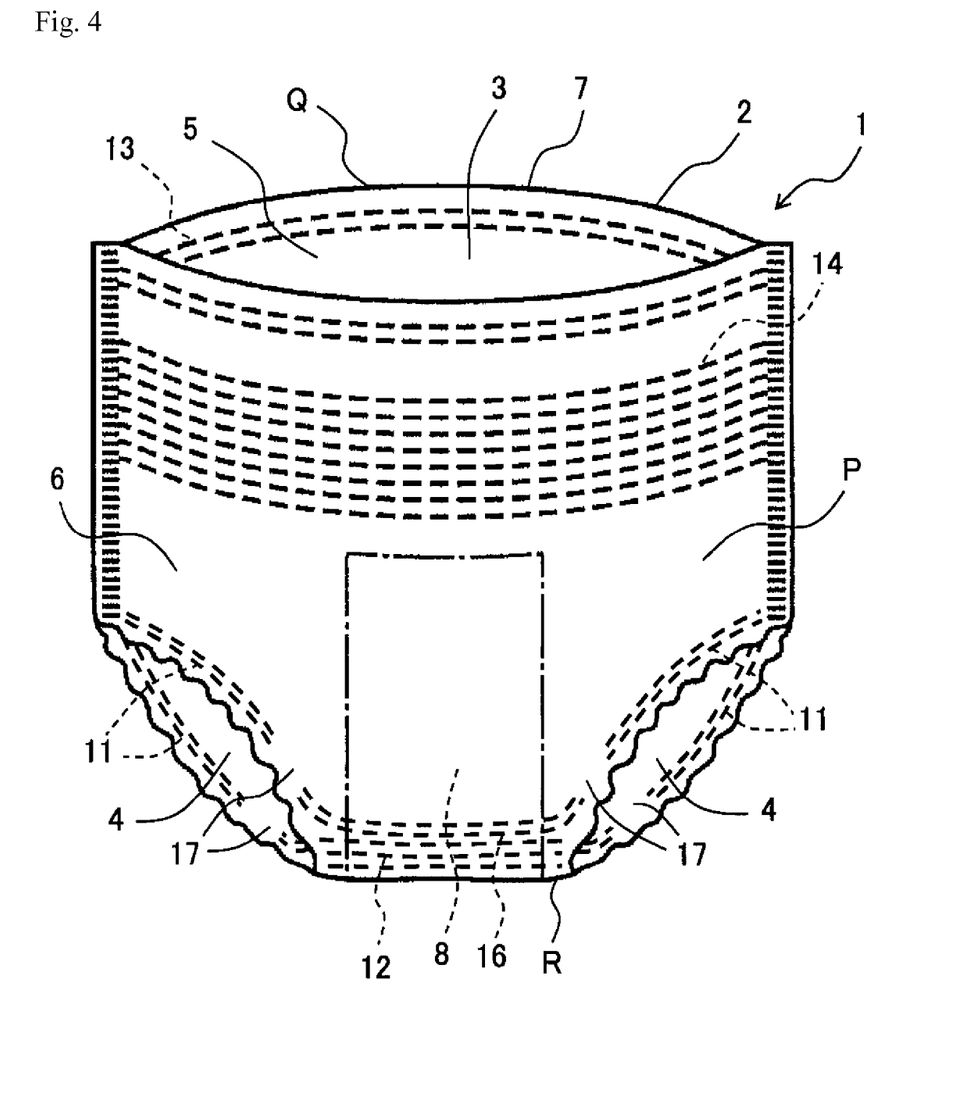
FIG. 4 shows a perspective view of a disposable pants-type diaper of the present invention according to a second embodiment.
Figure 5:
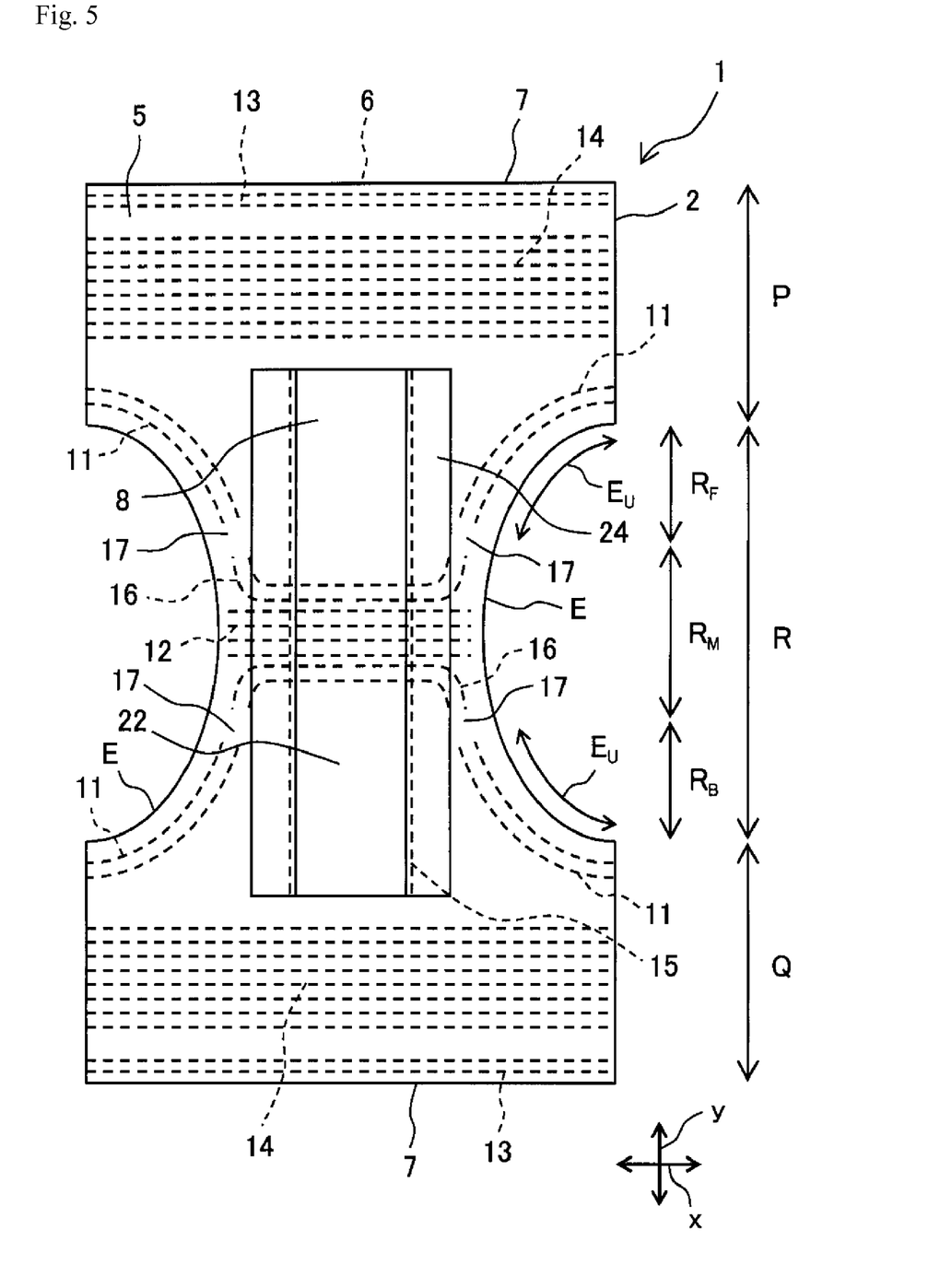
FIG. 5 shows a plan view of the disposable pants-type diaper shown in FIG. 4 in a developed state in which a front portion and a back portion are disjoined.

Next, a second embodiment of the disposable pants-type diaper of the present invention is explained referring to FIGS. 4 and 5. The disposable pants-type diaper according to the second embodiment comprises a first elastic means disposed along an upper part of an edge of both leg openings; a second elastic means disposed in a middle part in a front-back direction of a crotch portion, extending in a diaper width direction to near the edge of the both leg openings, and having straight side edge portions; and a third elastic means disposed in the middle part in the front-back direction of the crotch portion, adjacent to and substantially parallel to the second elastic means, and having side edge portions extending upward along the edge of the leg openings.

FIG. 4 shows a perspective view of the disposable pants-type diaper of the present invention according to the second embodiment. FIG. 5 shows a plan view of the disposable pants-type diaper shown in FIG. 4 in a developed state in which a front portion and a back portion are disjoined. In the following, the description of parts overlapping the first embodiment is omitted.

In the second embodiment, third elastic means are additionally disposed with respect to the first embodiment. First elastic means 11 are disposed along the upper parts $E_u$ of the edge E of the leg openings 4. A second elastic means 12 is disposed in the middle part $R_M$ in the front-back direction of the crotch portion R, extends in the diaper width direction x to near the edge E of the leg openings 4, and has straight side edge portions. Third elastic means 16 are disposed in the middle part $R_M$ in the front-back direction of the crotch portion R, adjacent to and substantially parallel to the second elastic means 12, and have side edge portions extending upward along the edge E of the leg openings 4, thereby providing non-elastic regions 17 along the edge E of the leg openings 4 between the first elastic means 11 and the third elastic means 16. In the second embodiment, the four first elastic means 11 are disposed along the upper parts $E_u$ of the edge E of the leg openings 4, and the two third elastic means 16 are disposed adjacent to the second elastic means 12 at the front and back sides of the second elastic means 12, respectively, thereby forming the four non-elastic regions 17 along the edge E of the both leg openings 4.

Figure 6:
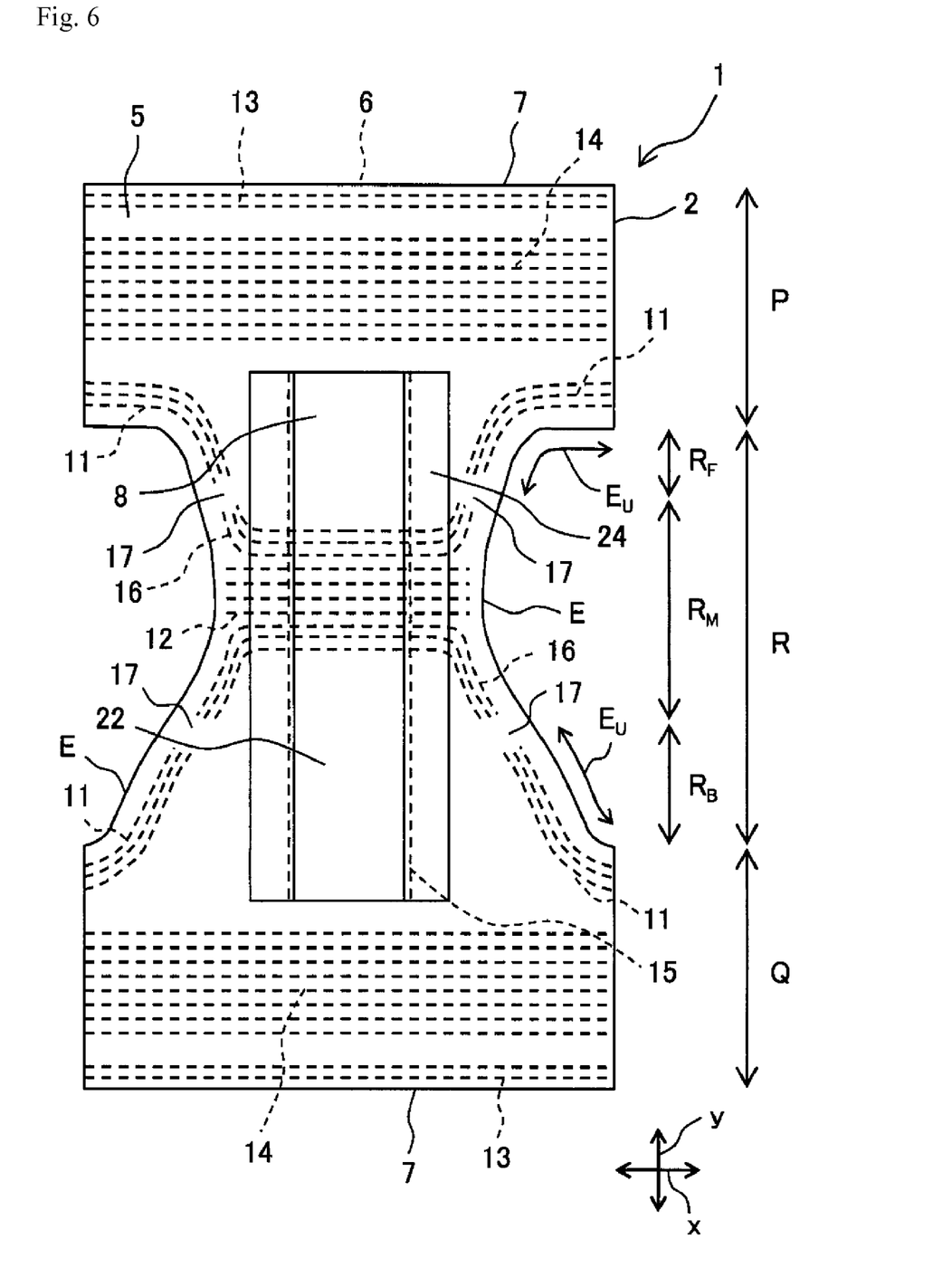
FIG. 6 shows an embodiment in which the second elastic means is unevenly located toward the front side of the crotch portion, with respect to the second embodiment.

FIG. 6 shows an embodiment (a modified second embodiment) in which the second elastic means 12 is unevenly located toward the front side of the crotch portion and the shapes of the edge E of the leg openings are changed with respect to the second embodiment. In the modified second embodiment, the edge E of the leg openings 4 is formed such that the diaper less covers the vicinity of an inguinal regions of a wearer on the front side and more covers a hip of the wearer. When the second elastic means 12 is unevenly located toward the front side of the crotch portion, the fitting property in the vicinity of genitals is enhanced, resulting in enhancing the effect of preventing leakage of urine and the like easily. Further, when the edge E of the leg opening 4 is formed as in the modified second embodiment, the fitting property to a hip is enhanced and a wearer easily moves his or her legs.

Figure 7:
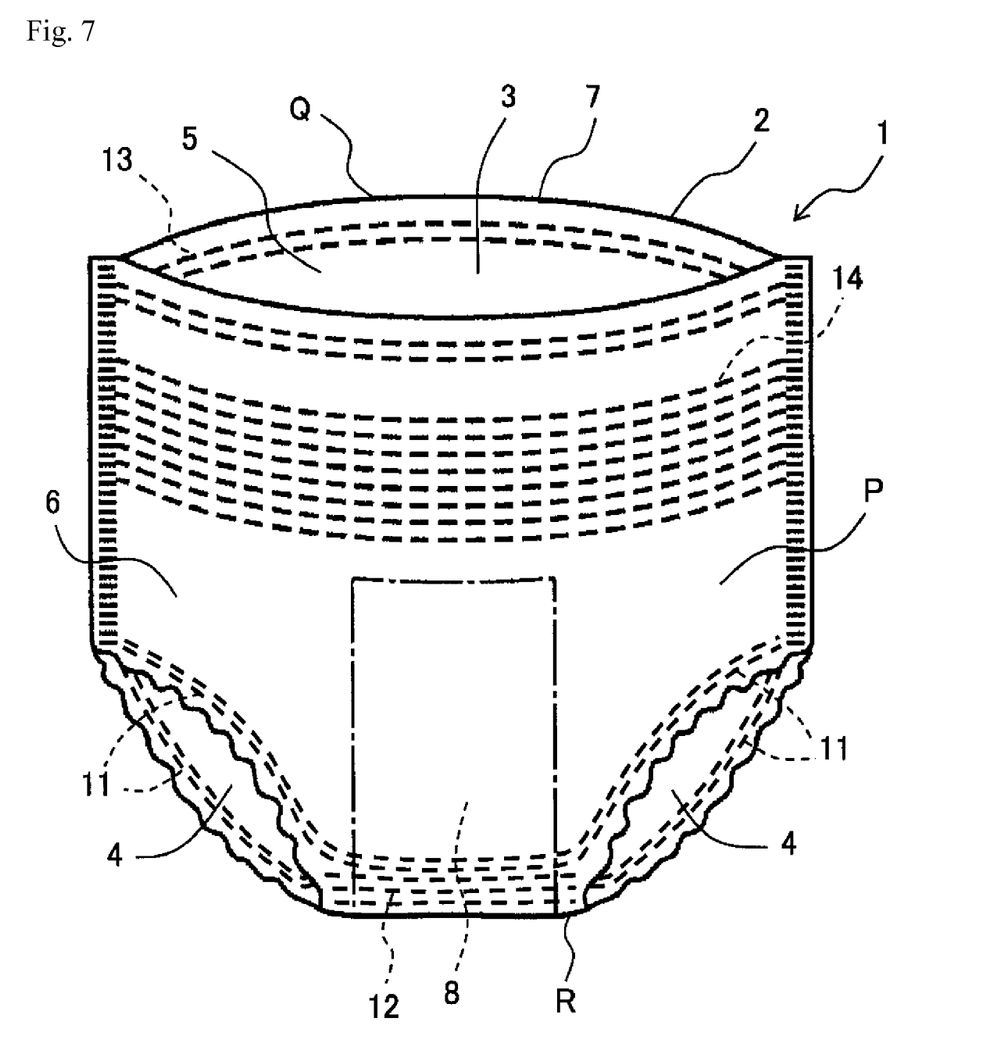
FIG. 7 shows a perspective view of a disposable pants-type diaper of the present invention according to a third embodiment.
Figure 8:
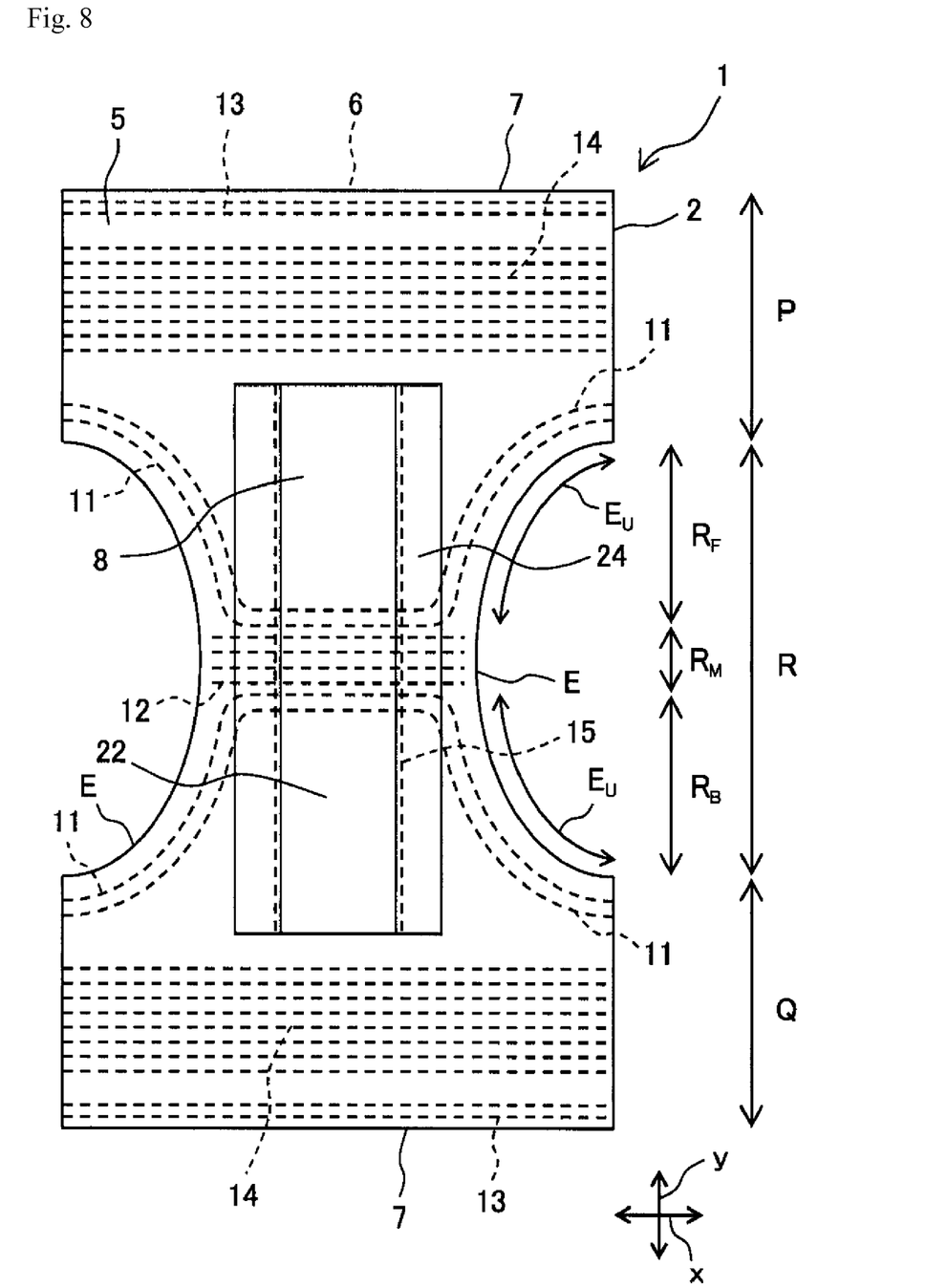
FIG. 8 shows a plan view of the disposable pants-type diaper shown in FIG. 7 in a developed state in which a front portion and a back portion are disjoined.

Next, a third embodiment of the disposable pants-type diaper of the present invention is explained referring to FIGS. 7 and 8. FIG. 7 shows a perspective view of the disposable pants-type diaper of the present invention according to the third embodiment. FIG. 8 shows a plan view of the disposable pants-type diaper shown in FIG. 7 in a developed state in which a front portion and a back portion are disjoined. In the following, the description of parts overlapping the first embodiment is omitted.

In the third embodiment, first elastic means 11 are disposed continuously so as to extend across a crotch portion R and along an edge E of the leg openings 4, with respect to the first embodiment. First elastic means 11 are disposed so as to extend across the crotch portion R and along the upper parts $E_u$ of the edge E of the leg openings 4. A second elastic means 12 is disposed in the middle part $R_M$ in the front-back direction of the crotch portion R, extends in the diaper width direction x to near the edge E of the leg openings, and has straight side edge portions 4.

The invention claimed is:

1. A disposable pants-type diaper comprising:
    a diaper main body including a front portion, a back portion, and a crotch portion positioned between the front portion and the back portion, and having a waist opening and a pair of leg openings formed by joining the front portion and the back portion;
    an absorbent core disposed in the crotch portion;
    a first elastic means disposed along an upper part of an edge of each of the leg openings;
    a second elastic means disposed in a middle part in a front-back direction of the crotch portion, wherein an entirety of the second elastic means extends linearly in a diaper width direction to near the edge of each of the leg openings; and
    at least one third elastic means disposed in the middle part in the front-back direction of the crotch portion so as to be adjacent to and substantially parallel to the second elastic means, the third elastic means having side edge portions extending upward along the edge of each of the leg openings such that a non-elastic region is provided along the edge of each of the leg openings between the first elastic means and the third elastic means.

2. The disposable pants-type diaper according to claim 1, wherein the second elastic means has side edge portions, each side edge portion of the second elastic means being located in an area within 15 mm from the edge of a respective one of the leg openings.

3. The disposable pants-type diaper according to claim 1, wherein the first elastic means, the third elastic means and the non-elastic region are formed by providing an elastic member continuously so as to extend across the crotch portion and along the edge of each of the leg openings, and cutting the elastic member along the edge of each of the leg openings.

4. The disposable pants-type diaper according to claim 1, wherein the first elastic means comprises four portions, a first pair of the four portions being disposed along the upper part of the edge of one of the leg openings and a second pair of the four portions being disposed along the upper part of the edge of the other of the leg openings, and wherein the at least one third elastic means includes one elastic means disposed adjacent to the second elastic means at a front side thereof and one elastic means disposed adjacent to the second elastic means at a back side thereof, such that the non-elastic region provided along the edge of each of the leg openings comprises a pair of non-elastic regions provided along the edge of each of the leg openings.

5. The disposable pants-type diaper according to claim 1, wherein at least one of the first elastic means, the second elastic means and the third elastic means comprises a plurality of elastic members.

6. The disposable pants-type diaper claim 1, wherein the second elastic means comprises a plurality of elastic members.

7. The disposable pants-type diaper according to claim 1, further comprising:

rising flaps disposed along opposite side edges of the absorbent core, respectively, such that the rising flaps are spaced apart from each other in the diaper width direction.

\* \* \* \* \*